(12) United States Patent
Morgan

(10) Patent No.: US 9,884,051 B2
(45) Date of Patent: Feb. 6, 2018

(54) DEMETHYLPENCLOMEDINE ANALOGS AND THEIR USE AS ANTI-CANCER AGENTS

(71) Applicant: Dekk-Tec, Inc., New Orleans, LA (US)

(72) Inventor: Lee Roy Morgan, New Orleans, LA (US)

(73) Assignee: Dekk-Tec, Inc., New Orleans, LA (US)

(*) Notice: Subject to any disclaimer, the term of this patent is extended or adjusted under 35 U.S.C. 154(b) by 0 days.

(21) Appl. No.: 15/238,144

(22) Filed: Aug. 16, 2016

(65) Prior Publication Data
US 2016/0354354 A1   Dec. 8, 2016

Related U.S. Application Data

(62) Division of application No. 13/402,660, filed on Feb. 22, 2012, now Pat. No. 9,422,241, which is a division of application No. 12/085,789, filed as application No. PCT/US2006/047526 on Dec. 12, 2006, now Pat. No. 8,124,596.

(60) Provisional application No. 60/750,211, filed on Dec. 13, 2005.

(51) Int. Cl.
| A01N 45/00 | (2006.01) |
| A61K 31/56 | (2006.01) |
| A61K 31/4412 | (2006.01) |
| C07D 213/64 | (2006.01) |
| C07D 213/68 | (2006.01) |
| A61K 45/06 | (2006.01) |

(52) U.S. Cl.
CPC .......... A61K 31/4412 (2013.01); A61K 45/06 (2013.01); C07D 213/64 (2013.01); C07D 213/68 (2013.01)

(58) Field of Classification Search
USPC ..................................................... 514/169
See application file for complete search history.

(56) References Cited

U.S. PATENT DOCUMENTS

| 4,717,726 A | 1/1988 | Tobol |
| 6,235,761 B1 | 5/2001 | Hartman et al. |
| 6,376,518 B1 | 4/2002 | Struck |
| 6,391,893 B1 | 5/2002 | Struck et al. |
| 6,495,571 B1 | 12/2002 | Struck et al. |

FOREIGN PATENT DOCUMENTS

| CA | 2596752 | 8/2006 |
| WO | WO00/43009 | 7/2000 |
| WO | WO00/43010 | 7/2000 |
| WO | WO2006/083930 | 8/2006 |

OTHER PUBLICATIONS

Gura et. al. (Science, 1997, 278:1041-1042).*
Johnson et. al. (British Journal of Cancer, 2001, 84:1424-1431).*
Arthur, Michael A., "Carbonate rocks deconstructed," *Nature*, vol. 460, pp. 698-699 (Aug. 6, 2009).
Cannon, J. G., Chapter Nineteen in Burger's Medicinal Chemistry and Drug Discovery, Fifth Edition, vol. 1: Principles and Practice, Wiley-Interscience, pp. 783-802 (1995).
Ettmayer et al., Lessons Learned from Marketed and Investigational Prodrugs, *Journal of Medicinal Chemistry*, vol. 47, No. 10, pp. 2393-2404 (May 6, 2004).
Examiner's Report from the Australian Patent Office for Australian Patent Application No. 2006326506, dated Apr. 28, 2011.
Examiner's Report from the Canadian Intellectual Property Office for Canadian Patent Application No. 2,632,618, dated Aug. 1, 2012.
Examiner's Report from the Canadian Intellectual Property Office for Canadian Patent Application No. 2,632,618, dated Apr. 8, 2013.
Examiner's Report from the European Patent Office for EP Patent Application No. 06 845 337.2, dated Apr. 25, 2013.
Final Office Action from the U.S. Patent and Trademark Office for U.S. Appl. No. 12/085,789, dated Oct. 24, 2011.
Final Office Action from the U.S. Patent and Trademark Office for U.S. Appl. No. 13/402,660, dated Sep. 15, 2014.
Final Office Action from the U.S. Patent and Trademark Office for U.S. Appl. No. 13/402,660, dated Feb. 29, 2016.
International Preliminary Report on Patentability for PCT/US2006/047526 (dated Jun. 18, 2008).
International Search Report in International Application No. PCT/US2006/047526 dated Sep. 20, 2007.
Knauth, L. Paul et al., "The late Precambrian greening of the Earth," *Nature*, vol. 460, pp. 728-732 (Aug. 6, 2009).
Morgan, Lee Roy et al., "4-Demethyl-4-cholesteryloxycarbonylpenclomedine (DM-CHOC-PEN) Phase I Clinical Tr," Grant 1R43CA132257-01A1 from National Cancer Institute, Abstract Only, 1 page (document marked Aug. 1, 2008).
Morgan et al., "Carbonate and carbamate derivatives of 4-demethylpenclomedine as novel anticancer agents," *Cancer Chemother Pharmacol*, vol. 64, No, 4, pp. 829-835 (Sep. 2009).
Morgan, Lee Roy et al., "Derivatives of Demethylpenclomedine: Anticancer Agents," Grant 5R44CA085021-04 from National Cancer Institute, Abstract Only, 1 page (document marked May 1, 2000).
Notice of Reasons for Rejection from the Japanese Patent Office for Japanese Patent Application No. 2008-545766, dated Jul. 9, 2012.
Notice of Reasons for Rejection from the Japanese Patent Office for Japanese Patent Application No. 2008-545766, dated Feb. 13, 2013, and English Translation.

(Continued)

*Primary Examiner* — Marcos Sznaidman
(74) *Attorney, Agent, or Firm* — Klarquist Sparkman, LLP

(57) ABSTRACT

This disclosure concerns novel demethylpenclomedine analogs. Also disclosed are pharmaceutical compositions and methods for using such compositions to treat hyperproliferative disorders. In one embodiment the analogs are represented by the formula

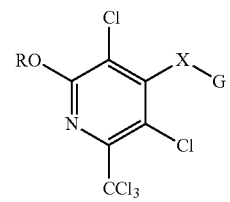

17 Claims, No Drawings

(56) References Cited

OTHER PUBLICATIONS

Office Action from the European Patent Office for European Patent Application No. 06845337.2, dated Apr. 22, 2009.
Office Action from the European Patent Office for European Patent Application No, 06845337.2, dated Jun. 30, 2011.
Office Action from the U.S. Patent and Trademark Office for U.S. Appl. No. 12/085,789, dated Mar. 29, 2011.
Office Action from the U.S. Patent and Trademark Office for U.S. Appl. No. 13/402,660, dated Apr. 25, 2014.
Office Action from the U.S. Patent and Trademark Office for U.S. Appl. No. 13/402,660, dated Oct. 9, 2015.
Restriction Requirement from the U.S. Patent and Trademark Office for U.S. Appl. No. 12/085,789, dated Oct. 21, 2010.
Restriction Requirement from the U.S. Patent and Trademark Office for U.S. Appl. No. 13/402,660, dated Jan. 22, 2014.
Struck et al., "Acyl derivatives of demethylpenclomedine, an antitumor-active, non-neurotoxic metabolite of penclomedine," *Cancer Chemother Pharmacol*, vol. 48, pp. 47-52 (2001).
Struck and Waud, "Thiolo-, thiono- and dithiocarbonate and thiocarbamate derivatives of demethylpenclomedine as novel anticancer agents," *Cancer Chemother Pharmacol*, vol. 57, pp. 180-184 (2006).
Stryer (Biochemistry, 4th Edition), W.H. Freeman and Co., New York pp. 702-77 (1995).
Tiwari et al., "Synthesis and Antitumor Activity of Several New Analogues of Penclomedine and Its Metabolites," *J. Med. Chem.*, vol. 45, pp. 1079-1085 (2002).
Waud et al., "4-Demethylpenclomedine, an Antitumor-active, Potentially Nonneurotoxic Metabolite of Penclomedine," *Cancer Research*, vol. 57, pp. 815-817 (1997).
Written Opinion for PCT/US2006/047526 (dated Sep. 20, 2007).

\* cited by examiner

DEMETHYLPENCLOMEDINE ANALOGS AND THEIR USE AS ANTI-CANCER AGENTS

CROSS REFERENCE TO RELATED APPLICATION

This application is a Divisional of U.S. patent application Ser. No. 13/402,660, filed Feb. 22, 2012, which is a Divisional of U.S. patent application Ser. No. 12/085,789, filed Feb. 3, 2009, now U.S. Pat. No. 8,124,596, which is the §371 U.S. National Stage of International Application No. PCT/US2006/047526, filed Dec. 12, 2006, which was published in English under PCT Article 21(2), which claims the benefit of U.S. Provisional Patent Application No. 60/750,211, filed Dec. 13, 2005, all of which are incorporated herein by reference.

FIELD

This disclosure concerns novel demethylpenclomedine analogs. Also disclosed are pharmaceutical compositions and methods for using such compositions to treat hyperproliferative disorders.

BACKGROUND

Brain cancers resist standard cancer treatments. For example, the currently preferred treatment for cancer is surgical resection. However, few brain cancers are operable. As a result, these tumors typically are treated with radiation therapy. Unfortunately, cranial radiotherapy is dose-limited and often only has a palliative effect. Chemotherapeutic agents when administered by systemic routes usually have difficulty penetrating the blood-brain barrier, which yields a poor anti-cancer response.

The compound 3,5-dichloro-4,6-dimethoxy-2-(trichloromethyl)-pyridine, commonly referred to as penclomedine (PEN), has demonstrated promising activity against brain cancers, but in all clinical trials dose-limiting neurotoxicity was observed. Specifically, dose related neurotoxicity consisting of dysmetria, ataxia, and vertigo were observed when patients with advanced solid tumors were treated with penclomedine administered as a one hour infusion for 5 consecutive days.

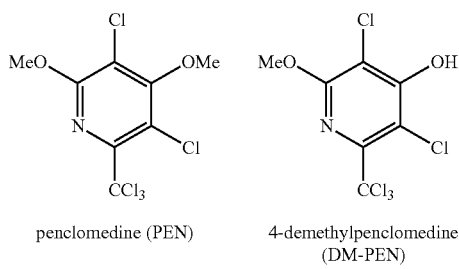

penclomedine (PEN)          4-demethylpenclomedine (DM-PEN)

As demonstrated in U.S. Pat. No. 6,391,893 to Struck et al., PEN is a prodrug that is metabolized to an active alkylating agent in vivo. One of PEN's metabolites, 4-demethylpenclomedine (DM-PEN) has been shown to be more active than PEN in various central nervous system (CNS) cancer models. Some early studies (Waud et al. *Cancer Res.* 1997, 57, 815-817) indicated that DM-PEN lacked the neurotoxicity of the parent compound. Unfortunately, however, the initial promise of DM-PEN has not been fulfilled. Thus, there exists a continuing need for anticancer agents of increased efficacy and decreased side effects.

SUMMARY

Disclosed herein are novel therapeutic agents that are effective against hyper-proliferative disorders. Examples of the disclosed agents are represented by the formula

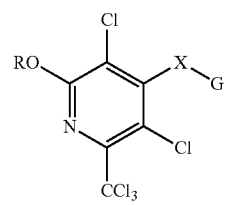

wherein R is a lower alkyl group;
X is O or $N(R^1)$
G is one of $-C(O)OR^2$; $-C(O)SR^2$; $-C(O)NR^3R^4$;
$R^1$ is hydrogen or optionally substituted aliphatic;
$R^2$ is optionally substituted aliphatic, optionally substituted aromatic, optionally substituted heterocyclic, optionally substituted aryl, including heteroaromatic groups, optionally substituted aralkyl or combinations thereof; and
$R^3$ and $R^4$ independently are H, optionally substituted aliphatic, optionally substituted aromatic, optionally substituted heterocyclic, optionally substituted heteroaromatic, optionally substituted aralkyl or combinations thereof.

In one embodiment, pharmaceutical compositions are disclosed that include one or more of the anti-hyperproliferative agents described above. In one aspect of this embodiment, the compositions can include one or more therapeutic agents other than those described by the formula above, such as another anti-hyperproliferative agent, for use in combination therapy.

In another embodiment, methods for treating mammalian subjects, such as human subjects, having hyperproliferative disorders are disclosed. Such methods can employ one or more of the compounds and compositions described above.

The foregoing and other objects, features, and advantages of the invention will become more apparent from the following detailed description.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance can but need not occur, and that the description includes instances where said event or circumstance occurs and instances where it does not.

"Acyl" refers group of the formula RC(O)— wherein R is an organic group.

The term "aliphatic" includes alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers an aliphatic group that is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "aralkyl" refers to an alkyl group that is substituted with one or more aryl groups (described below). A particular example of an aralkyl group is a benzyl group.

The term "aryl" refers to any carbon-based aromatic group including, but not limited to, benzene, naphthalene, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carbonate" refers to a group of the formula —OC(O)O—. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative" refers to a compound or portion of a compound that is derived from or is theoretically derivable from a parent compound.

The term "subject" includes both human and veterinary subjects.

The term "treating a disease" refers to inhibiting the full development of a disease or condition, for example, in a subject who is at risk for a disease such as a tumor (for example, a leukemia or a lymphoma). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

"Neoplasia" refers to the process of abnormal and uncontrolled cell growth. Neoplasia is one example of a hyperproliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Certain embodiments disclosed herein are directed to the treatment of metastatic cancers of the brain. Such metastatic cancers are referred to by the primary tumor site as well as the secondary site. For example, breast cancer that has metastasized to the brain is referred to as "metastatic breast cancer to the brain."

The term "pharmaceutically acceptable salt or prodrug" is used herein to describe any pharmaceutically acceptable form (e.g., ester, phosphate ester, salt of an ester or a related group) of a disclosed compound, which, upon administration to a subject, provides or produces an active compound. Pharmaceutically acceptable salts include those derived from pharmaceutically acceptable inorganic or organic bases and acids. In particular, suitable salts include those derived from alkali metals such as potassium and sodium, alkaline earth metals such as calcium and magnesium, among numerous other acids well known in the pharmaceutical art.

The term "prodrug" also is intended to include any covalently bonded carriers that release a disclosed compound or a parent thereof in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a hydroxy, amino, or sulfhydryl group functionalized with any group that is cleaved to yield the corresponding hydroxyl, free amino, or free sulfhydryl group, respectively. Examples of prodrugs include, without limitation, compounds having a hydroxy, amino and/or sulfhydryl group acylated with an acetate, formate, and/or benzoate group.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

Reference will now be made in detail to the presently preferred embodiments of the disclosed compounds, compositions and methods.

I. Compounds

In one embodiment, the disclosed compounds include those represented by the formula

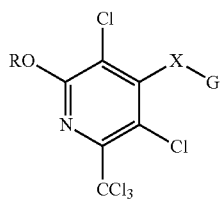

wherein R is an optionally substituted lower alkyl group;
X is O or N(R$^1$)
G is one of —C(O)OR$^2$; —C(O)SR$^2$; —C(O)NR$^3$R$^4$;
R$^1$ is hydrogen or optionally substituted aliphatic;
R$^2$ is optionally substituted aliphatic, optionally substituted heterocyclic, optionally substituted aryl, including heteroaromatic groups, optionally substituted aralkyl or combinations thereof; and
R$^3$ and R$^4$ independently are H, optionally substituted aliphatic, optionally substituted aromatic, optionally substituted heterocyclic, optionally substituted heteroaromatic, optionally substituted aralkyl or combinations thereof.

With reference to the formula above, R is an optionally substituted lower alkyl group. Examples of such groups include, inter alia, haloalkyl groups, as well as branched lower alkyl groups. Particular R groups include, without limitation, methyl, trifluoromethyl, ethyl, propyl, isopropyl, butyl, sec-butyl, isobutyl and tert-butyl.

As indicated in the formula above, X and G, together, can comprise a carbonate, carbamate, urea, thiocarbamate or a thiocarbonate moiety. Certain G groups include an optionally substituted aliphatic, aralkyl or aryl substituent. In particular compounds wherein X and G together form a carbonate or thiocarbonate (—OC(O)OR$^2$; —OC(O)SR$^2$), such groups are represented by R$^2$, and wherein X and G together form a carbamate or urea, such groups are represented by R$^3$ and/or R$^4$ (—OC(O)NR$^3$R$^4$; —N(R$^1$)C(O) NR$^3$R$^4$). Examples of suitable substituents of such groups include, without limitation, nitro, halo and lower alkyl groups. In one embodiment, G includes a haloalkyl group, such as a trifluoromethyl group. In particular embodiments, G comprises a hydrophobic moiety—without being limited to theory it is currently believed that such hydrophobic G groups facilitate the crossing of the blood brain barrier. Examples of such hydrophobic groups include, without limitation perfluoroalkyl groups and aryl groups. For example, particular G groups include halobenzyl moieties, such as ortho-fluoro and ortho-chlorobenzyl moieties. G also can include other cyclic groups, including polycyclic systems and heterocyclic systems. Examples of compounds wherein G comprises a polycyclic group include hydrophobic polycyclic groups, such as those wherein the polycyclic group is a steroid. For example, in one embodiment G comprises a testosterone derivative, such as a group of the formula

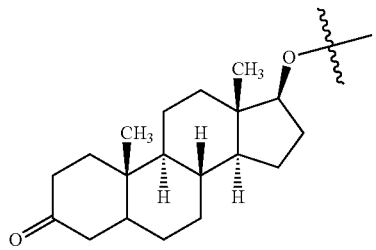

In one such embodiment, G represents a group of the formula

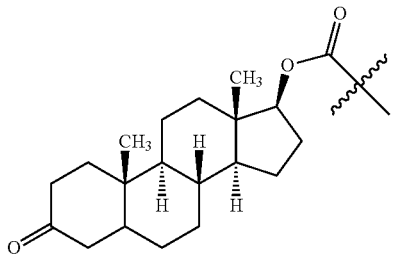

In another embodiment, G comprises a cortisone derivative; examples of such groups include those wherein R$^2$, R$^3$ and/or R$^4$ represent a steroid derivative of the formula

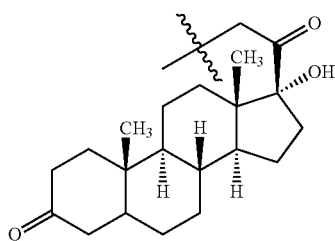

In other embodiments, G comprises an estrogen derivative, such as an estriol, adiol or estrone derivative. In one embodiment such G groups include a moiety of the formula

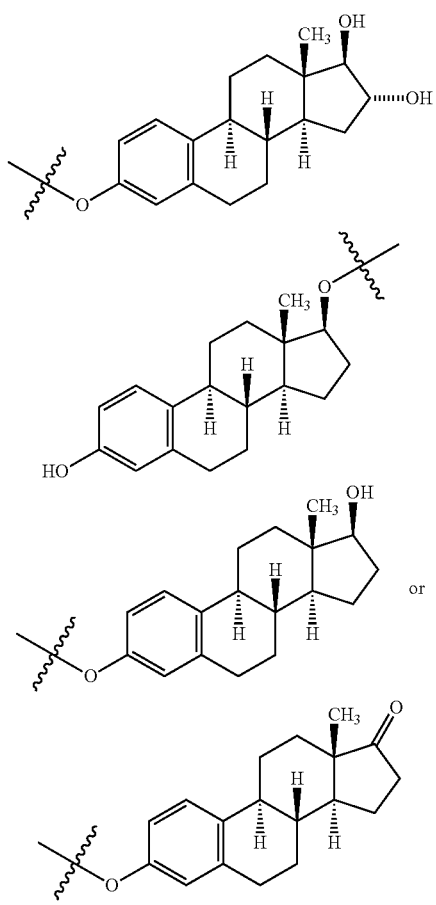

Similarly, in certain embodiments G comprises a steroid group wherein $R^2$, $R^3$ and/or $R^4$ represent a group of the formula

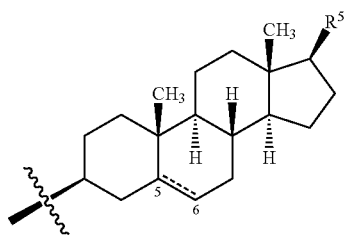

wherein $R^5$ is an optionally substituted aliphatic group, such as an optionally substituted branched or unbranched lower alkyl group. In one example, wherein $R^2$ has the formula above, G represents a group of the formula

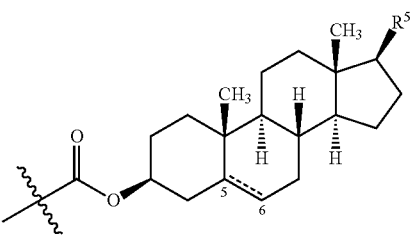

wherein $R^5$ is as described above. As indicated in the steroid structures above, C5 and C6 may be connected via a single or a double bond. In a particular embodiment G comprises a cholesterol derivative having the formula

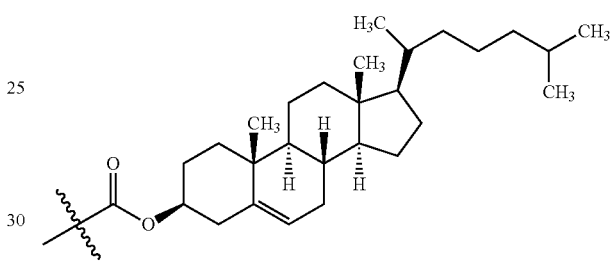

In other embodiments, G comprises a dehydroepiandrosterone derivative. For example, in one embodiment, G represents

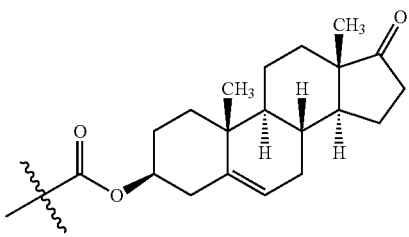

In certain embodiments, $R^2$, $R^3$ and/or $R^4$ include a heterocyclic group. For example, in certain compounds G has the formula —C(O)NR³R⁴ and $R^3$ and $R^4$ together comprise a cyclic group. In one aspect G is represented by the formula

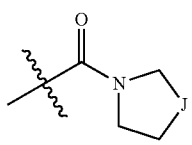

wherein J is one of $(CH_2)_n$; N; O; —CH₂O—; or —CH₂N($R_6$)—; wherein $R_6$ is H, acyl, lower alkyl or aralkyl and n is 1 or 2. For example, $R^3$ and $R^4$ together can form a five-membered ring, such as a pyrrolidinyl moiety or a six-membered ring, such as a piperidinyl, piperazinyl or morpholinyl moiety.

In one embodiment, disclosed carbonate and carbamate compounds have a formula set forth in Table 1.

TABLE 1

| | X | R² |
|---|---|---|
| (structure with Cl, H₃CO, N, Cl, CCl₃ substituents on pyridine ring, with X-C(=O)-OR² group) | O | Me |
| | O | Et |
| | O | cholesteryl |
| | O | o-fluorobenzyl |
| | O | o-chlorobenzyl |
| | O | benzyl |
| | O | p-nitrobenzyl |
| | O | p-nitrophenyl |
| | O | phenyl |
| | O | n-octyl |
| | —NH— | benzyl |
| | —NH— | ethyl |
| | —N(CH₃)— | benzyl |

Additional selected embodiments of disclosed carbamate and carbonate compounds are represented in Table 2.

TABLE 2

| | R³ | R⁴ |
|---|---|---|
| (structure with Cl, H₃CO, N, Cl, CCl₃ substituents on pyridine ring, with O-C(=O)-NR³R⁴ group) | H | Me |
| | H | Et |
| | H | cholesteryl |
| | Me | Me |
| | Me | phenyl |
| | phenyl | phenyl |
| | morpholino | |

II. Compositions and Methods

Another aspect of the disclosure includes pharmaceutical compositions prepared for administration to a subject and which include a therapeutically effective amount of one or more of the currently disclosed compounds. Disclosed also are methods for administering the disclosed compounds and compositions. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. The relationship of these factors to determining a therapeutically effective amount of the disclosed compounds is understood by those of ordinary skill in the art.

Methods are disclosed herein for treating conditions characterized by abnormal or pathological proliferative activity. Such conditions that can be treated according to the disclosed method include those characterized by abnormal cell growth and/or differentiation, such as cancers and other neoplastic conditions. Typical examples of hyperproliferative disorders that can be treated using the disclosed compounds and compositions include brain cancer, breast cancer, bladder cancer, bone cancer, cervical cancer, colon cancer, central nervous system cancer, esophageal cancer, gall bladder cancer, gastrointestinal cancer, head and neck cancer, Hodgkin's Disease, non-Hodgkin's lymphomas, laryngeal cancer, leukemia, lung cancer, melanoma, neuroblastoma, ovarian cancer, pancreatic cancer, prostate cancer, rectal cancer, retinoblastoma, stomach cancer, testicular cancer and Wilms' tumor.

In a particular embodiment, methods are provided for treating metastatic cancers to the brain, including, for example, metastatic breast cancer to the brain. Additional examples of metastatic cancers to the brain that can be treated using the compounds and compositions disclosed herein include lung cancer, sarcoma, colorectal cancer, lymphoma and leukemia.

The therapeutically effective amount of the compound or compounds administered can vary depending upon the desired effects and the factors noted above. Typically, dosages will be between about 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and a subject's body weight.

Alternatively, dosages are calculated based on body surface area and from about 1 mg/m² to about 200 mg/m², such as from about 5 mg/m² to about 100 mg/m² will be administered to the subject per day. In particular embodiments administration of the therapeutically effective amount of the compound or compounds comprises administering to the subject from about 5 mg/m² to about 50 mg/m², such as from about 10 m g/m² to about 40 mg/m² per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

It is specifically contemplated in some embodiments that delivery of the disclosed compounds is via an injected and/or implanted drug depot, for instance comprising multivesicular liposomes such as in DepoFoam (SkyePharma, Inc, San Diego, Calif.) (see, for instance, Chamberlain et al, *Arch. Neuro.* 1993, 50, 261-264; Katri et al, *J. Pharm. Sci.* 1998, 87, 1341-1346; Ye et al., *J. Control Release* 2000, 64, 155-166; and Howell, *Cancer J.* 2001, 7, 219-227). In particular embodiments the disclosed anticancer agents are administered directly to a neoplasm, such as by injection and/or implantation. For example, the agents can be formed into a pellet and implanted directly into a tumor. In one example, a 10 mg pellet containing 97% DM-CHOC-PEN was prepared by pressing it with 3% of an additive selected from lysine, stearic acid and/or povidone. Pellets can be manufactured, for example, in dosages of from about 0.5 mg to about 50 mg of active compound, such as in 0.5 mg, 1 mg, 5 mg, 10 mg and 25 or 50 mg doses. Such pellets can be inserted or implanted directly into a target region. Adjustments in pellet concentrations may be made according to the observed physical properties (such as dissolution rates) and animal toxicity. Therapeutically effective doses can be determined by known means, and doses to be administered can be varied depending on the condition being treated, or the severity of a disease.

In contrast with PEN and DM-PEN, it is currently believed that certain of the disclosed compounds, such as DM-CHOC-PEN, do not require activation by the liver to be effective. Such compounds are particularly suitable for direct administration to a tumor. Alternatively, these compounds can be administered via a systemic route with subsequent transport to the target tissue. In addition, certain embodiments of the disclosed compounds are significantly less neurotoxic than PEN and DM-PEN.

It is contemplated that in some embodiments the disclosed compounds are used with other types of treatments, such as cancer treatments. For example the disclosed inhibitors may be used with other chemotherapies, including those employing an anti-proliferative agent, such as, without limitation, microtubule binding agent, a toxin, a DNA intercalator or cross-linker, a DNA synthesis inhibitor, a DNA and/or RNA transcription inhibitor, an enzyme inhibitor, a gene regulator, enediyne antibiotics and/or an angiogenesis inhibitor. Additionally, the disclosed compounds can be used in combination with radiation therapy, surgery, or other modalities of cancer therapy.

"Microtubule binding agent" refers to an agent that interacts with tubulin to stabilize or destabilize microtubule formation thereby inhibiting cell division. Examples of microtubule binding agents that can be used in conjunction with the presently disclosed compounds include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art. For example, suitable epothilones and epothilone analogs for incorporation into the present compounds are described in International Publication No. WO 2004/018478, which is incorporated herein by reference. Taxoids, such as paclitaxel and docetaxel are currently believed to be particularly useful as therapeutic agents in the presently disclosed compounds. Examples of additional useful taxoids, including analogs of paclitaxel are taught by U.S. Pat. No. 6,610,860 to Holton, U.S. Pat. No. 5,530,020 to Gurram et al, and U.S. Pat. No. 5,912,264 to Wittman et al. Each of these patents is incorporated herein by reference.

Suitable DNA and/or RNA transcription regulators for use with the disclosed compounds include, without limitation, actinomycin D, daunorubicin, doxorubicin and derivatives and analogs thereof also are suitable for use in combination with the presently disclosed compounds.

DNA intercalators, cross-linking agents and alkylating agents that can be used in combination therapy with the disclosed compounds include, without limitation, cisplatin, carboplatin, oxaliplatin, mitomycins, such as mitomycin C, bleomycin, chlorambucil, cyclophosphamide, isophosphoramide mustard and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors for use in combination with the presently disclosed compounds include, without limitation, camptothecin, etoposide, formestane, trichostatin and derivatives and analogs thereof.

Suitable therapeutics for use with the presently disclosed compounds that affect gene regulation include agents that result in increased or decreased expression of one or more genes, such as, without limitation, raloxifene, 5-azacytidine, 5-aza-2'-deoxycytidine, tamoxifen, 4-hydroxytamoxifen, mifepristone and derivatives and analogs thereof.

The term "angiogenesis inhibitor" is used herein, to mean a molecule including, but not limited to, biomolecules, such as peptides, proteins, enzymes, polysaccharides, oligonucleotides, DNA, RNA, recombinant vectors, and small molecules that function to inhibit blood vessel growth. Angiogenesis inhibitors are known in the art and examples of suitable angiogenesis inhibitors include, without limitation, angiostatin K1-3, staurosporine, genistein, fumagillin, medroxyprogesterone, SFTI-1, suramin, interferon-alpha, metalloproteinase inhibitors, platelet factor 4, somatostatin, thromobospondin, endostatin, thalidomide, and derivatives and analogs thereof.

Other therapeutic agents, particularly anti-tumor agents, that may or may not fall under one or more of the classifications above, also are suitable for administration in combination with the presently disclosed compounds. By way of example, such agents include adriamycin, apigenin, erlotinib, gefitinib, temozolomide, rapamycin, topotecan, carmustine, melphalan, mitoxantrone, irinotecanetoposide, tenoposide, zebularine, cimetidine, and derivatives and analogs thereof.

The compounds disclosed herein may be administered orally, topically, transdermally, parenterally, via inhalation or spray and may be administered in dosage unit formulations containing conventional non-toxic pharmaceutically acceptable carriers, adjuvants and vehicles.

Typically, oral administration or administration via implantation or intravenously, such as via injection is preferred. However the particular mode of administration employed may be dependent upon the particular disease, condition of patient, toxicity of compound and other factors as will be recognized by a person of ordinary skill in the art.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In one embodiment, preferred therapeutic agents are identified herein by assessing their in vitro cytotoxic activity against cultured model cancer cell lines. For example, certain disclosed therapeutic agents exhibit in vitro IC50 values against a model cell line of less than about 10 micrograms/mL, such as from about 0.1 micrograms/mL to less than about 5 micrograms/mL, in particular from about 0.05 micrograms/mL to less than about 2.5 micrograms/mL. Suitable cell lines against which the disclosed compounds may be assessed are well known to those of skill in the art and include, by way of example, KG breast CA, LM breast CA and 9 L rat glioma. One example of the disclosed compounds, DM-CHOC-PEN, exhibited in vitro $IC_{50}$ values of 0.7±0.4, 1.0±0.5 and 1.1±0.4 micrograms/mL against KG breast CA, LM breast CA and 9 L rat glioma, respectively. The KG breast cancer explants were obtained from surgical biopsies of chest wall metastases from breast cancer. The patient had failed on extensive standard and experimental chemo/hormone and radiation therapy protocols. Minced biopsy specimens were grown in RPMI plus 10% FBS with antibiotics at 37° C. and 5% $CO_2$ atmosphere. DM-CHOC-PEN was tested at 0.5-5 μg/mL concentrations in medium and incubated for 24 hrs. $IC_{50}$ values were 1.1+/−0.5 μg/mL. DM-PEN is not active in vitro and requires prior activation per the liver.

III. EXAMPLES

The foregoing disclosure is further explained by the following non-limiting examples.

Example 1

Synthesis of DM-PEN Derivatives

This example describes a general procedure for the synthesis of carbonate and carbamate derivatives of 4-demethylpenclomedine (DM-PEN). DM-PEN (1 equivalent; obtained from the National Cancer Institute) in dry methylene chloride was treated with one equivalent of triethylamine in one batch. The resulting yellow solution was treated drop wise with stirring at room temperature with one equivalent of an acyl chloride, an alkyl or aryl chloroformate or a dialkyl-, diaryl-, or alkylaryl carbamoyl chloride in dry methylene chloride. The reaction mixture was stirred 1 hour at room temperature, and the solvent was removed by evaporation in vacuo. The residue was triturated with acetone and filtered to remove triethylamine hydrochloride. The filtrate was concentrated in vacuo to a small volume and separated by preparative thin layer chromatography (TLC) on silica gel in a hexane:methylene chloride solvent (1:1,v/v). The major UV-visible band was collected and eluted with acetone, and the eluate evaporated to dryness in vacuo. The residue was characterized by mass spectral (FABMS), NMR (H) and elemental (CHN) analysis. If the product was not analytically pure, it was separated again by preparative TLC for subsequent re-analysis. Most products did not require a second TLC purification step, and a high yield was obtained. Using 1 gram of DM-PEN, sufficient product was obtained and sufficient for tumor experiments evaluated at three dose levels, including its $LD_{10}$.

This general procedure was used to synthesize the following structures:

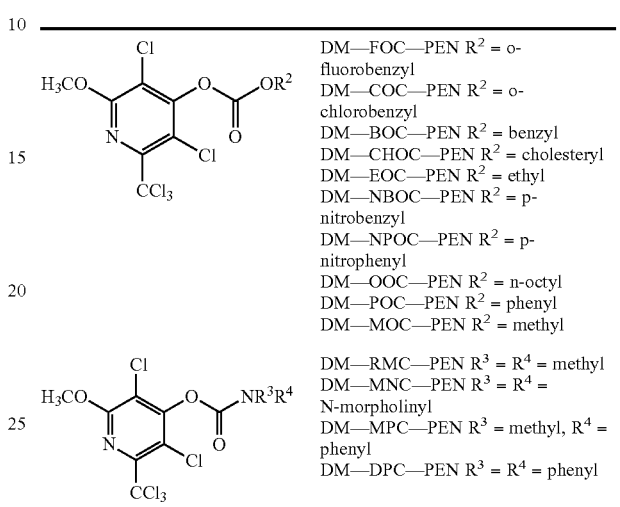

DM—FOC—PEN $R^2$ = o-fluorobenzyl
DM—COC—PEN $R^2$ = o-chlorobenzyl
DM—BOC—PEN $R^2$ = benzyl
DM—CHOC—PEN $R^2$ = cholesteryl
DM—EOC—PEN $R^2$ = ethyl
DM—NBOC—PEN $R^2$ = p-nitrobenzyl
DM—NPOC—PEN $R^2$ = p-nitrophenyl
DM—OOC—PEN $R^2$ = n-octyl
DM—POC—PEN $R^2$ = phenyl
DM—MOC—PEN $R^2$ = methyl
DM—RMC—PEN $R^3$ = $R^4$ = methyl
DM—MNC—PEN $R^3$ = $R^4$ = N-morpholinyl
DM—MPC—PEN $R^3$ = methyl, $R^4$ = phenyl
DM—DPC—PEN $R^3$ = $R^4$ = phenyl

Example 2

Synthesis of 4-Demethyl Cholesteryloxycarbonylpenclomedine

This example describes the synthesis of 4-demethyl cholesteryloxycarbonylpenclomedine according to the scheme illustrated below.

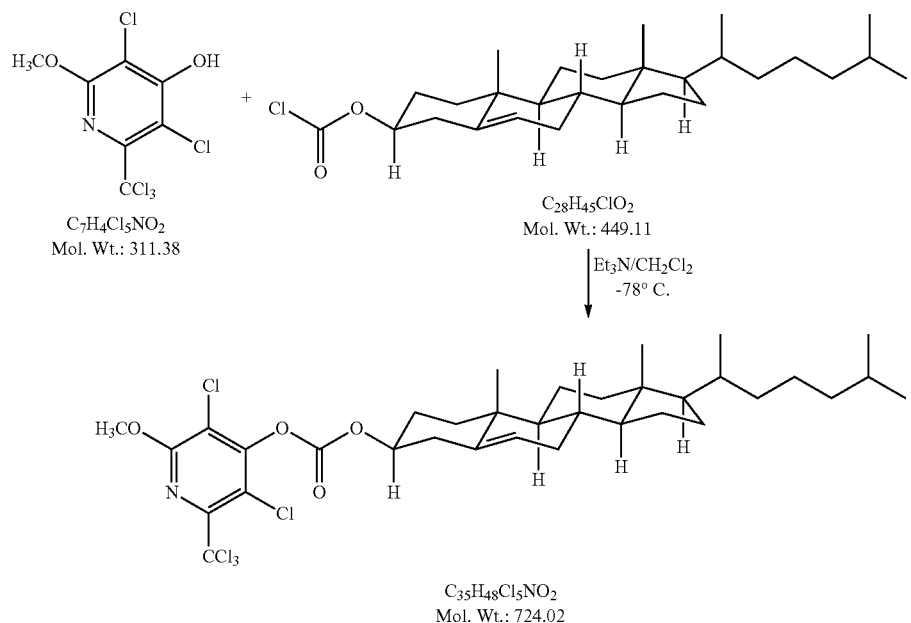

A solution of 4-demethylpenclomedine (12.44 g) and triethyla ine (12 mL) dissolved in methylene chloride (100 mL) and cooled in a dry-ice/acetone bath. A methylene chloride solution of cholesteryl chloroformate (19.0 g in 75 mL) was slowly added dropwise over the course of 45 minutes. The reaction mixture was stirred at −78° C. for 3 hours. The solvent was removed to dryness under reduced pressure at room temperature (not to exceed 30° C.). The resulting yellow solid was slurred in ice-cold acetone (100 mL) and filtered. The yellow solid were broken, and the solid was again washed with ice-cold acetone (4×20 mL). The resulting solid was transferred to a 500 mL beaker, and 120 mL cold water was added to the solid. The solid suspension was stirred at room temperature for no more than 30 minutes. The white solid was then filtered and washed with water (3×50 mL) followed by ice-cold acetone (2×15 mL). The product was air-dried, and the resulting pure white solid material collected. The yield was 21.0 g (91%); $^1$H-NMR and $^3$C-NMR agreed with the illustrated structure.

Example 3

Analog Antitumor Evaluation In Vivo vs. Human Tumor Xenografts

Orthotopic human tumor models used for evaluation of the DM-PEN derivatives in vivo included the MX-1 breast tumor, D54 and the U251 CNS tumors. The breast tumor was implanted in the mammary fat pad and the CNS tumors in the cerebrum. All evaluations were conducted in AAALAC-approved facilities supervised by veterinarians and using protocols approved by NCI for such studies.

MX-1 tumor, 30 to 40 mg tumor fragments were implanted sc in mouse mammary fat pad, and tumors will be allowed to grow until they were ca. 100 mg., which usually required 7-14 days. Doses of the DM-PEN derivatives were 60, 90 and 135 mg/kg administered IP to groups of 5 mice on a qd 1-5 schedule; these doses and schedule have been shown to be optimal for PEN and DM-PEN, yielding cures. The formulations consisted of a smooth suspension in Tween 80/saline. DM-PEN was used as a positive control, and if toxicity >LD$_{10}$ or <LD$_{10}$ was observed for the three doses for any of the derivatives, those derivatives were re-evaluated at appropriately lower or higher doses as necessary to provide a dose response that includes an ca. LD$_{10}$ dose. Antitumor activity was assessed on the basis of tumor growth delay in comparison to a vehicle-treated control (saline), tumor regressions (partial and complete) and tumor-free survivors. Experiments were continued until the control tumors (10 mice) attain a size of ca. 1 g.

U251 and D54 tumors, 10$^6$ cultured cells in 0.03 ml volume were injected via a 25-gauge stainless steel 0.25 inch needle into the right cerebrum with angling toward the center of the brain. Tumor take-rate was typically ca. 100%, and treatment was initiated ca. 5 days after implantation on a qd 1-5 schedule at doses of 60, 90 and 135 mg/kg administered IP, to groups of 5 mice. Doses varied to include an ca LD$_{10}$ as described above for the MX-1 tumor. BCNU was used clinically to treated advanced gliomas and will be used as a positive control at optimal doses of 17, 10 and 6 mg/kg on a qd 1-5 schedule, since it is also the clinical standard for brain tumors and is very active against this tumor model. DM-PEN at 60, 90 and 135 mg/kg on the same schedule was included as a comparative control. Antitumor activity was assessed on the basis of survival, with the medial day of death of the controls (10 mice) typically being ca. 30-35 days. The in vivo tumor inhibition results are recorded in Table 3.

TABLE 3

DM-PEN analogs vs. U251 GBM*

| Compound | Tumor Type | ILS** | LTC*** |
|---|---|---|---|
| DM-PEN | U251 GBM | 13 | 0 |
| DM-Ac-PEN | | 38-44 | — |
| DM-MOC-PEN | | 28 | — |
| DM-BOC-PEN | | 54 | — |
| DM-CHOC-PEN | | 29 | 1/5 |
| DM-DMC-PEN | | 21 | — |
| DM-MNC-PEN | | 33 | — |
| DM-MPC-PEN | | 26 | — |
| DM-DPC-PEN | | 13 | — |

*GMM—glioblastoma multiformi
**ILS %—percentage increased length of survival in days vs. control.
***LTC—long-term cure - days (>30-35 days).

As recorded in Table 3, DM-CHOC-PEN produced the highest increase in life span (% ILS) in comparison to other DM-PEN analogs evaluated simultaneously. DM-CHOC-PEN yielded 1/5 (20%) long-term survivors and resulted in no weight loss, The effects of DM-PEN and DM-CHOC-PEN also were compared at various doses against three different cancer lines. The results are recorded in Table 4. All ratios were within confidence limits. Specifically, DM-CHOC-PEN in U251 human glioma xenografts implanted intracranially (IC) yielded 1/5 (20%) long-term survivors and resulted in no weight loss. BCNU was used as a control. The MX-1 breast cancer, which is very resistant to anticancer agents and an excellent model with which to select potentially active new agents for anticancer screening trials, was implanted IC in mice. The resulting activities demonstrated superiority activity of DM-CHOC-PEN vs. DM-PEN. Gratifyingly, the DM-CHOC-PEN treatment regimen did not demonstrate neurotoxicity in the animal studies.

TABLE 4

Activity of DM-CHOC-PEN and DM-PEN vs. Intracerebral (IC) Implanted Human Xenografts in Mice

| | DM-CHOC-PEN | | | DM-PEN | | |
|---|---|---|---|---|---|---|
| Tumor | Dose (mg/kg) | % Increase in Life Span (% ILS) | % Long Term Survivors (% LTS) | Dose (mg/kg) | % ILS | % LTS |
| U251 Glioblastoma | 135 | +29 | 20 (1/5 CR) | 90 | 17 | 0/5 |
| D54 Glioblastoma | 200 | +3 | 20 (1/5 CR) | — | | — |
| MX-1 Breast Cancer | 25 | +6 | 17 (1/6 CR) | 60 | 12 | 0/5 |
| | 50 | +20 | | | | |

Implant: 10$^6$ cells
Treatment Route: Intraperitoneal
Schedule: q1d × 5d
Species: Athymic NCr/nu mice - female, Charles River With reference to Table 4, DM-CHOC-PEN is compared with DM-PEN against U251 tumor cells in mice. % ILS was observed for the two agents in the U251 treated groups. The DM-CHOC-PEN treatment demonstrated superiority over the DM-PEN treatment. The DM-CHOC-PEN treated animals had a two-fold increase in survival (compared to DM-PEN) with a tumor burden reduction of a log₁₀ 7. The dosing was IP daily×5 days. BCNU control—was effective with +92% ILS.

As indicated by Table 4, DM-CHOC-PEN also was compared with DM-PEN against D54 glioblastoma. The drugs were administered IP daily for 5 days, after tumor implantation. There was statistical improvement in activity for DM-CHOC-PEN's % LTS.

With continued reference to Table 4, DM-PEN and DM-CHOC-PEN were compared with daily dosing for 5 days. Based on the preclinical antitumor activities, for the U251 glioma DM-CHOC-PEN yielded ⅕ (20%) long-term survivor and resulted in no weight loss. Similarly, for MX-1 tumors, DM-CHOC-PEN gave ⅙ (17%) long-term survivors and no weight loss. DM-PEN did not produce any complete responders. LTS->90 days.

The results recorded in Tables 3 and 4 indicate that DM-CHOC-PEN is better than or equivalent to DM-PEN. Moreover, the results demonstrate that DM-CHOC-PEN administered intraperitoneally penetrates brain tissue and inhibits the growth of growing intracranial cancers.

Example 4

This example describes the toxicity of DM-CHOC-PEN to mice as administered via intravenous injections and oral gavage. For the intravenous study, the dose range-finding phase consisted of five treatment groups (one male mouse/group) that received the test article as a single dose at respective dose levels of 50 (dose volume of 5 mL/kg), 100 (dose volume of 10 mL/kg), 150 (dose volume of 15 mL/kg), 250 (dose volume of 25 mL/kg), and 500 mg/kg (intended total dose volume of 50 mL/kg). The 500 mg/kg dose was intended to be a split dose that was to be administered in equal fractions (25 mL/kg/dose) approximately four hours apart (mortality precluded administration of the second portion of the dose). An additional group (one male mouse) served as the control and received the vehicle, soybean oil, at a dose volume of 25 mL/kg using the same route of administration as the treated groups. On Day 4, following the three-day observation period, all surviving dose range-finding animals were euthanized and discarded. Based on the immediate deaths noted in the dose-range finding phase at 0, 100, 250 and 500 mg/kg (the 500 mg/kg animal died after the first half of the planned split dose) and the apparent toxicity/effects of the soybean oil vehicle, the vehicle for the definitive main study phase was changed to 0.3% Klucel+ 0.3% to 3.3% Tween® 80 and the dose levels chosen for the main study phase were 0, 50, 100, 200, 400, and 600 mg/kg.

The main study phase consisted of five treatment groups (five mice/sex/group) that received a single dose of the test article at respective dose levels of 50, 100, 200, 400, and 600 mg/kg. An additional group (five mice/sex) served as the control and received the vehicle, 0.3% Klucel+1.92% Tween® 80, using the same dosing regimen as the treated groups. All doses were at a constant volume of 25 mL/kg.

Observations for mortality, morbidity, and the availability of food and water were conducted twice daily for all animals. Observations for clinical signs were conducted daily during the study (approximately one and four hours post-dose on Day 1 and then once daily). Body weights were measured on all animals after receipt, prior to randomization and on Day 1. In addition, body weights were measured for all surviving main study phase animals on Days 7 and 14. Macroscopic evaluations were performed on each main study phase animal at necropsy (Day 15).

Mortality results from the IV administration generally displayed a typical dose-response effect (with the exception of one death at 50 mg/kg), with DM-CHOC-PEN being slightly more toxic in males than in females at the two highest doses. No animals died at 0 or 100 mg/kg, 1 of 10 animals died at both 50 and 200 mg/kg, 7 of 10 animals died at 400 mg/kg and 8 of 10 animals died at 600 mg/kg. Various clinical signs reflecting treatment-related effects were noted in both sexes, oftentimes in a generally dose-dependent manner. These clinical signs included decreased activity, rapid/difficult/slow/shallow breathing, limbs splayed, tremors and skin cold to touch. The deaths at 40 0and 600 were of a very immediate nature, occurring within minutes or less post-dose, with no clinical signs exhibited prior to death. While transient incidences of rapid breathing were also noted in a couple of control animals, a definitive relationship to the vehicle was unclear. No definitively clear treatment—related body effects were noted in those mice surviving the 14-day observation period when compared with controls. No macroscopic findings were noted in any animal at necropsy. Based on the conditions and findings of this study, the intravenous $LD_{10}$ of DM-CHOC-PEN was calculated to be 136 mg/kg (95% confidence limits could not be calculated) in mice (combined sexes), while the intravenous $LD_{50}$ was calculated to be 385 mg/kg (95% confidence limits of 298 to 502 mg/kg). Acute intravenous toxicity study results are presented in Table 5

TABLE 5

Acute IV Toxicity in the Mouse - MPI Study
(Single Dose)

| Route | Dose (mg/kg) | Number and Sex | Observations |
| --- | --- | --- | --- |
| IV | 0 | 5M 5F | No deaths |
|  | 50 | 5M 5F | 0 M and 1 F died |
|  | 100 | 5M 5F | No deaths |
|  | 200 | 5M 5F | 0 M and 1 F died |
|  | 400 | 5M 5 F | 4M and 3 F died |
|  | 600 | 5M 5F | 5 M and 3 F died |

Sub-acute oral mouse toxicity study was conducted at MPI Research, Mattawan, Mich., under GLP conditions in male/female mice. The study evaluated DM-CHOC-PEN in a 8% Tween-80® Neobee®-1053 solution administered daily for five days at doses of 0, 800, 1000, 1200, 1500 and 2000 mg/kg.

Only one death occurred at 800 mg/kg on day 2 after dosing. All animals demonstrated some degree of lethargy and unkept appearance. No seizures noted. Similar body appearances were noted with the controls. The therapeutic studies revealed responses in the 150-225 mg/kg dosing ranges.

Example 5

This example describes the acute toxicity of DM-CHOC-PEN in dogs. An acute study was performed in adult Beagle dogs, which consisted of: DM-CHOC-PEN administered once IV. Sixteen (16) adult beagle dogs (8 male and 8 female) divided into three groups received a single intravenous injection of DM-CHOC--PEN. The DM-CHOC-PEN was administered in 0.3% Klucel+1.92% Tween® 80. The results are recorded in Table 6.

TABLE 6

Acute IV Toxicity in the Dog

| Route/Schedule | Dose (mg/kg) | Number and Sex | Observations |
|---|---|---|---|
| IV once | 0 | 2M 2 F | No deaths |
|  | 10 | 2 M 2 F | No deaths |
|  | 20 | 2 M 2 F | No deaths |
|  | 30 | 2 M 2 F | No deaths |

Based on the conditions and findings of this study, a single intravenous injection of DM-CHOC-PEN to respective groups of beagle dogs at dose levels of 10, 20, and 30 mg/kg caused no effects that were directly related to the test article, as all the findings noted on study were instead attributable to the 0.3% Klucel+1.92% Tween® 80 vehicle used.

Table 7 summarizes the toxic effects of single dose acute administrations in mice and dogs. This table includes three investigations on the acute toxicity performed in mice and dogs.

TABLE 7

DM-CHOC-PEN Medial Lethal Dose Summary (27) (Single Dose)

| Species and Strain | Number and Sex | Method | $LD_{50}$ (g/kg) | Time* |
|---|---|---|---|---|
| Mouse, (Sprague-Dawley)[Crl: $CD^R$ (BR)] | 36 M 36 F | IV | 0.39 | 2-14 days |
| Mouse, CD2F1 | 12 F | IV | 0.39 | 21 days |
| Dog, Beagle | 8 M 8 F | IV | >0.03 | 10 days |

*The time until the last death is reported first, followed by the length of the study.

Based on the preclinical animal studies described above, DM-CHOC-PEN is considered to be a minimally toxic alkylating agent with a steep therapeutic range. The mean toxic dose (MTD) in humans should be about 1/10 the $LD_{10}$ in mice or 39 mg/m²/d.

TABLE 8

Estimated Comparable Human Intravenous Dosages

| Species | Acute IV ($LD_{10}$) | Comparable Human IV Dosage |
|---|---|---|
| Mouse | 136 mg/kg | 39 mg/m² |
| Dog | >30 mg/kg | >600 mg/m² |

Example 6

This example describes the treatment of tumors via implantation of a DM-CHOC-PEN pellet. To prepare the tumors, rats were implanted with 10⁶ 9 L rat glioma cells either intracerebrally or intraperitoneally. The implanted cells were observed to grow well, for example by expanding centrifically into normal brain tissue. After 5 days a 10 mg pellet of 97% DM-CHOC-PEN with lysine and stearic acid was implanted in the tumor. No toxicity was observed over 6 weeks. However, tumor cells within approximately 10 cells from the pellet were killed. Visual observation of the implanted pellets revealed dissolution of the pellet in the tumor. Histological exam revealed granules of the drug pellet along blood vessels and in dead tumor cells. Angiogenesis into the drug pellet was observed, with the drug being absorbed into the tumor and the consequent death of the tumor cells.

While this disclosure has been described with an emphasis upon particular embodiments, it will be apparent to those of ordinary skill in the art that variations of the particular embodiments can be used, and it is intended that this disclosure can be practiced otherwise than as specifically described herein. Features and characteristics, or the disclosed compounds, chemical moieties, compositions, methods described in conjunction with other particular features herein are to be understood to be applicable to any other aspect, embodiment, or example disclosed herein.

Accordingly, this disclosure includes all modifications encompassed within the spirit and scope of the disclosure as defined by the claims.

Moreover, in view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

The invention claimed is:

1. A method for treating a subject having brain and/or breast cancer, comprising administering to the subject a therapeutically effective amount of a compound of the formula

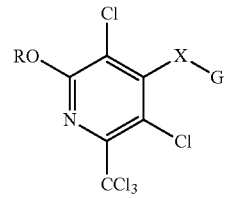

or a pharmaceutically acceptable salt,
wherein R is methyl;
X is O;
G is —C(O)OR²; and
R² is a steroid ring structure.

2. The method of claim 1, comprising administering from about 1 mg/m² to about 200 mg/m² to the subject per day.

3. The method of claim 1, comprising administering from about 5 mg/m² to about 100 mg/m² to the subject per day.

4. The method of claim 1, comprising administering from about 10 mg/m² to about 50 mg/m² to the subject per day.

5. The method of claim 1, wherein the brain cancer comprises a brain tumor.

6. The method of claim 1, wherein the brain cancer comprises a metastatic cancer of the brain.

7. The method of claim 1, wherein the method comprises treating the subject for at least one of metastatic breast cancer and leukemia to the brain.

8. The method of claim 1, further comprising administering a second compound to the subject.

9. The method of claim 8, wherein the second compound is selected from microtubule binding agents, DNA intercalators, DNA alkylating agents, DNA cross-linkers, DNA synthesis inhibitors, DNA and/or RNA transcription inhibitors, enzyme inhibitors, gene regulators, enzymes, antibodies and angiogenesis inhibitors.

10. The method of claim 8, wherein the second compound is selected from erlotinib, gefitinib, temozolomide, paclitaxel, docetaxel, daunorubicin, cisplatin, carboplatin, oxaliplatin, colchicine, dolastatin 15, nocodazole podophyllotoxin, rhizoxin, vinblastine, vindesine, vinorelbine (navelbine), the epothilones, the mitomycins, bleomycin, chlorambucil, carmustine, melphalan, mitoxantrone, 5-fluoro-5'-deoxyuridine, camptothecin, SFTI-1, topotecan, irinotecanetoposide, teniposide, geldanamycin, methotrexate, adriamycin, actinomycin D, medroxyprogesterone, mifepristone, raloxifene, 5-azacytidine, 5-aza-2'-deoxycytidine, zebularine, tamoxifen, 4-hydroxytamoxifen, apigenin, rapamycin, angiostatin K1-3, L-asparaginase, staurosporine, genistein, fumagillin, endostatin, isophosphoramide mustard, thalidomide and analogs thereof.

11. The method of claim 8, further comprising administering a third compound to the subject, wherein the third compound is selected from the microtubule binding agents, DNA intercalators or cross-linkers, DNA synthesis inhibitors, DNA and/or RNA transcription inhibitors, enzyme inhibitors, gene regulators, enzymes, antibodies and angiogenesis inhibitors.

12. The method of claim 1, wherein administering comprises directly administering the compound to a tumor.

13. A method for treating a subject having brain and/or breast cancer, comprising administering to the subject a therapeutically effective amount of a compound of the formula

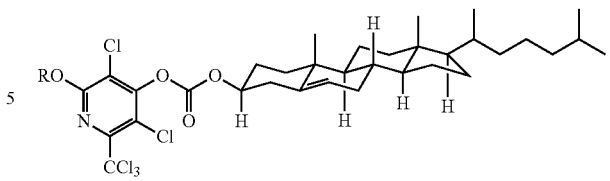

or a pharmaceutically acceptable salt thereof,
wherein R is a lower alkyl group optionally substituted with halogen.

14. The method of claim 13, comprising administering from about 1 mg/m$^2$ to about 200 mg/m$^2$ to the subject per day.

15. The method of claim 13, wherein the treating comprises treating a brain tumor.

16. The method of claim 13, wherein the method comprises treating the subject for at least one of metastatic breast cancer and leukemia to the brain.

17. The method of claim 13, further comprising administering a second compound to the subject, wherein the second compound is selected from microtubule binding agents, DNA intercalators, DNA alkylating agents, DNA cross-linkers, DNA synthesis inhibitors, DNA and/or RNA transcription inhibitors, enzyme inhibitors, gene regulators, enzymes, antibodies and angiogenesis inhibitors.

* * * * *

UNITED STATES PATENT AND TRADEMARK OFFICE
CERTIFICATE OF CORRECTION

PATENT NO. : 9,884,051 B2
APPLICATION NO. : 15/238144
DATED : February 6, 2018
INVENTOR(S) : Lee Roy Morgan Page 1 of 1

It is certified that error appears in the above-identified patent and that said Letters Patent is hereby corrected as shown below:

In the Specification

Column 3, Line 3, "refers group" should read --refers to a group--.

Column 15, Line 10, "solid were broken," should read --solid was broken,--.

Column 15, Line 61, "to treated" should read --to treat--.

Column 16, Line 36, "demonstrated superiority" should read --demonstrated superior--.

Column 20, Line 6, "or the disclosed" should read --of the disclosed--.

Signed and Sealed this
Tenth Day of May, 2022

Katherine Kelly Vidal
*Director of the United States Patent and Trademark Office*